United States Patent [19]
Watson

[11] 4,177,110
[45] Dec. 4, 1979

[54] METHOD FOR THE DISTILLATION OF VINYL AROMATIC COMPOUNDS USING POLYMERIZATION INHIBITORS WITH LOW-VOLATILITY

[75] Inventor: James M. Watson, Big Spring, Tex.

[73] Assignee: Cosden Technology, Inc., Big Spring, Tex.

[21] Appl. No.: 925,817

[22] Filed: Jul. 18, 1978

[51] Int. Cl.$^2$ .......................... B01D 3/34; C07C 7/18
[52] U.S. Cl. .......................................... 203/9; 203/49; 203/69; 203/91; 585/5
[58] Field of Search ...................... 203/8, 9, 49, 69, 91; 202/234; 260/669 A, 666.5

[56] References Cited

U.S. PATENT DOCUMENTS

| | | | |
|---|---|---|---|
| 2,445,941 | 7/1948 | Dreisbach | 203/9 |
| 2,607,720 | 8/1952 | Elwell et al. | 203/9 |
| 2,757,130 | 7/1956 | Burns | 203/8 |
| 3,239,433 | 3/1966 | Costolow | 203/8 |
| 3,513,078 | 5/1970 | Biarnais et al. | 203/49 |
| 3,515,647 | 6/1970 | Van Tassell et al. | 203/9 |
| 3,515,762 | 6/1970 | Koicle et al. | 203/9 |
| 3,629,076 | 12/1971 | Jones | 203/9 |
| 3,674,651 | 7/1972 | Otsuki et al. | 203/49 |
| 3,763,015 | 10/1973 | Morimoto et al. | 203/9 |
| 4,061,545 | 12/1977 | Watson | 203/9 |

Primary Examiner—Wilbur L. Bascomb, Jr.
Attorney, Agent, or Firm—Schwartz, Jeffery, Schwaab, Mack, Blumenthal & Koch

[57] ABSTRACT

A method and apparatus is disclosed for the distillation of readily polymerizable vinyl aromatic compounds with polymerization inhibitors of low volatility, particularly a phenothiazine (PZ)-tertiarybutylcatechol (TBC) polymerization inhibitor combination. The method comprises introducing a feed of impure vinyl aromatic compound into a typical distillation train comprising a first fractionation column, a recycle column, and a finishing column; introducing as a separate stream into the upper portion of said recycle column and into said first fractionation column an effective amount of the PZ-TBC inhibitor in a volatile aromatic hydrocarbon diluent; and then distilling the vinyl aromatic compound in the presence of oxygen to recover an overhead product of high purity vinyl aromatic compound and a bottoms fraction.

13 Claims, 2 Drawing Figures

METHOD FOR THE DISTILLATION OF VINYL AROMATIC COMPOUNDS USING POLYMERIZATION INHIBITORS WITH LOW-VOLATILITY

TECHNICAL FIELD OF THE INVENTION

The present invention relates to a process for the distillation of readily polymerizable vinyl aromatic compounds with polymerization inhibitors of low volatility. More particularly, the present invention relates to a process for the distillation of styrene, substituted styrene, divinylbenzene, and polyvinylbenzenes wherein the efficacy of polymerization inhibitors of low volatility in reducing the amount of said materials polymerized during distillation is increased over that obtained with conventional distillation methods, and wherein the rate of throughput for a given distillation apparatus may thereby be increased over the rate at which such apparatus may be operated in accordance with conventional methods.

BACKGROUND OF PRIOR ART

It is well known that vinyl aromatic compounds such as monomeric styrene, lower alkylated styrene, e.g., alpha-methyl styrene, and the like polymerize readily, and furthermore, that the rate of polymerization increases with increasing temperature. Inasmuch as vinyl aromatic compounds produced by common industrial methods contain impurities, these compounds must be subjected to separation and purification processes in order to be suitable for most types of further industrial use. Such separation and purification is generally accomplished by distillation. However, the heat required for distillation tends to increase the rate of polymerization, with higher distillation temperatures resulting in the formation of greater amounts of polymer.

Accordingly, many attempts have been made to develop distillation processes for vinyl aromatic monomers which do not suffer from the attendant problem of heat polymerization. Generally, these processes have utilized chemical inhibitors to prevent the polymerization of the vinyl aromatic monomers undergoing distillation. Although many compounds are effective for inhibiting the polymerization of vinyl aromatic compounds under differing conditions, e.g., storage, other purification techniques, etc., for a number of reasons which are not entirely understood in view of the diverse and unpredictable results obtained, only extremely few of these compounds have proved to be of any real utility for inhibiting vinyl aromatic polymerization under distillation conditions. Common inhibitors which have been utilized to prevent the polymerization of vinyl aromatic compounds under distillation conditions include 4-tert-butylcatechol (TBC) and hydroquinone. Additionally, sulfur has been widely employed as a polymerization inhibitor during the distillation of various vinyl aromatic compounds. However, while sulfur provides a reasonably effective inhibitor, its use in such distillation processes results in a highly significant disadvantage, the formation of a valueless waste material highly contaminated with sulfur in the reboiler bottoms of the distillation column which presents a significant pollution and waste removal problem. It thus remains a significant problem today that the amount of polymer formed in the distillation apparatus and in the high purity product recovered therefrom is substantially higher than desired and occasionally, that complete polymerization incurs inside the distillation apparatus. For example, in the process of distilling crude styrene (a mixture containing, inter alia, styrene, ethylbenzene, benzene, and toluene) to obtain high purity styrene, even when inhibited with sulfur and TBC, a styrene product is obtained which contains significant quantities of polymer which are difficult to separate from the product and are detrimental to the end use of such styrenes. Furthermore, the material recovered from the bottom or reboiler area of the distillation apparatus is a highly polluting sulfur-containing waste material which must be disposed of.

Recently, applicant has developed a distillation process using a phenothiazine (PZ)-tertiarybutylcatechol (TBC) chemical inhibitor system, described in U.S. Pat. No. 4,061,545, the entirety of which is herein incorporated by reference, which has proven to be particularly efficacious in producing high purity vinyl aromatic monomer with less polymer impurities than that obtained with conventional inhibitors. While the PZ-TBC inhibitor combination has been demonstrated to be superior to conventional inhibitors, applicant has found that an even higher efficacy can be attained by improving the distribution of this inhibitor combination within the recycle column of a typical distillation train. Surprisingly, applicant has found that in a conventional distillation train for styrene comprising a B-T column, an EB or recycle column, and a finishing column, approximately 80% of the polymer impurity is formed in the recycle column, with most of the remaining polymer being formed in the finishing column. Adequate polymerization inhibition in the recycle column is thus essential for elimination of the formation of undesirable polymer impurities. Heretofore, however, the PZ-TBC inhibitor has been amixed with a non-volatile hydrocarbon diluent, such as polyethylbenzene, which functions to reduce the viscosity of the bottoms material to facilitate the handling thereof and is introduced therewith into the lower portion of the recycle column. While this method of inhibitor addition provides adequate inhibitor distribution where a volatile inhibitor is employed, on the other hand, where a non-volatile inhibitor such as PZ-TBC is utilized, this method of addition limits the inhibitor distribution to the region of introduction into the column and below. Accordingly, this method of addition fails to provide inhibitor protection to the upper portion of the recycle column, resulting in the formation of a substantial portion of the total polymer impurity formed. Moreover, the PZ-TBC and polyethylbenzene mixture cannot simply be introduced higher into the recycle column because the polyethylbenzene will be carried into the overhead product and recycled therewith to an ethylbenzene dehydrogenation reactor where it is converted to divinylbenzene which poses a significant problem in plant operation. Accordingly, there exists a strong need for a distillation process using non-volatile inhibitors in general, and PZ-TBC in particular, in which the inhibitor distribution is optimized throughout the recycle column.

The prior art has long recognized the need for protecting a distillation system against unwanted polymer formation, and has accordingly developed many distillation processes wherein a polymerization inhibitor is introduced into the system. For example, U.S. Pat. Nos. 3,515,647 and 3,629,076 describe a distillation process wherein a TBC inhibitor is admixed with purified styrene in a reflux accumulator and introduced therewith, as reflux, into the top portion of a styrene finishing column. While this location for inhibitor addition provides adequate polymerization inhibition for the finishing column, addition of the inhibitor at this location fails to provide inhibitor protection in the recycle column where polymerization inhibition is most essential. Similarly, U.S. Pat. No. 3,448,015 teaches a distillation process for vinyl compounds using an aqueous nitrite solution as an inhibitor in which inhibitor addition is limited to the intermediate portion of the recycle column. With a non-volatile inhibitor such as PZ-TBC, such a system does not provide adequate polymerization inhibition in the critical upper portion of the recycle column.

Accordingly, it would be desirable to provide a distillation process which optimizes polymerization inhibitor distribution throughout a distillation system. It would be particularly desirable to provide a distillation process in which a PZ-TBC polymerization inhibitor is optimally distributed throughout the recycle column of a distillation system.

SUMMARY OF THE INVENTION

It is therefore an object of the present invention to provide a new and improved process for the distillation of readily polymerizable vinyl aromatic compounds.

It is an additional object of the present invention to provide a new and improved process for the distillation of readily polymerizable vinyl aromatic compounds, which process results in higher recovery of high purity unsaturated vinyl aromatic compounds and concomitantly in the production of less undesirable by-products.

A further object of the present invention resides in the provision of a new and improved process for the distillation of vinyl aromatic compounds which results in the production of substantially less polymerized material in the distillation apparatus.

It is also an object of the present invention to provide a new and improved process for the distillation of vinyl aromatic compounds which permits the distillation apparatus to be operated at an increased rate of throughput without a reduction in efficiency.

Yet, another object of the present invention is the provision of a new and improved process for the distillation of vinyl aromatic compounds wherein the polymerization efficiency of polymerization inhibitors of low volatility is improved.

Still another object of the present invention is the provision of a process for the distillation of vinyl aromatic compounds wherein the efficiency of a phenothiazine (PZ)-tertiarybutylcatechol (TBC) polymerization inhibitor combination is improved.

It is an additional object of the present invention to provide a new and improved process for the distillation of vinyl aromatic compounds which provides all of the foregoing ennumerated advantages in a vacuum distillation process. A specific object of the present invention resides in the provision of a new and improved distillation process wherein the distribution of a non-volatile PZ-TBC inhibitor is optimized throughout the recycle column of a typical distillation train.

In accomplishing the foregoing and other objects, there has been provided in accordance with the present invention a process for the distillation of a readily polymerizable vinyl aromatic compound, employing as a polymerization inhibitor the combination of phenothiazine (PZ) and tertiarybutylcatechol (TBC), comprising introducing a feed of impure vinyl aromatic compound into a distillation train comprising a recycle column and a finishing column; introducing as a separate stream into the upper portion of the recycle column an effective amount of the PZ-TBC inhibitor combination in a volatile aromatic hydrocarbon diluent; and then distilling the vinyl aromatic compound in the presence of oxygen to recover from the distillation train an overhead product of high purity vinyl aromatic compound and a residual bottoms fraction.

Broadly, the present invention is advantageous for the distillation of any vinyl aromatic compound. However, in a preferred embodiment, the present invention provides a particularly advantageous process for the distillation of styrene. In this aspect of the process according to the present invention, a styrene feed is distilled in a conventional three column distillation train comprising a first fractionation column or B-T column, a recycle column, and a finishing column. In one embodiment, high purity benzene and toluene are first removed as an overhead product from the crude styrene feed by fractional distillation in the presence of an effective amount of the PZ-TBC inhibitor and oxygen. The bottoms product from this first distillation is then introduced into the recycle column. Simultaneously, an effective amount of PZ-TBC polymerization inhibitor in a volatile aromatic hydrocarbon diluent is introduced as a separate stream into the upper portion of the recycle column. The styrene bottoms are then distilled in the presence of oxygen, yielding an ethylbenzene overhead and a styrene-containing bottoms fraction which is subsequently subjected to distillation conditions in the presence of oxygen in the finishing column to produce a high purity styrene overhead product and a residual waste bottoms. Alternatively, the crude styrene feed may be introduced directly into the recycle column whereupon distillation produces a benzene, toluene, and ethylbenzene overhead product and a styrene-containing bottoms. It is a salient feature of both of these embodiments, however, that an effective amount of the PZ-TBC inhibitor in a volatile aromatic hydrocarbon diluent be introduced as a separate stream into the critical upper portion of the recycle column.

The amount of phenothiazine and TBC necessary to inhibit polymerization of vinyl aromatic compounds may vary over a broad range depending upon various factors of the distillation process such as, for example, temperature, amount of reflux, if any, pressure, residence time, etc.. Typically, however, it has been found that an amount of inhibitor between about 5 ppm and 200 ppm of phenothiazine and between about 1 ppm and about 160 ppm of TBC is sufficient to substantially inhibit polymerization of vinyl aromatic compounds under normal distillation conditions, e.g., approximately 115° C.

Through the use of the process according to the present invention, the amount of polymerization occurring within the distillation apparatus is significantly reduced in comparison to conventionally employed methods. By improving the distribution of the non-volatile PZ-TBC polymerization inhibitor in the recycle column wherein approximately 80% of the total polymer impurity is formed, the amount of the desired distillation product is increased in proportion to the decrease in the amount of polymer formation. Additionally, the rate of operation of a given distillation apparatus may be increased in proportion to the decrease in the amount of polymer formation, permitting the rate of operation of a typical distillation apparatus to be increased over and above the rate of operation for the same apparatus utilizing a conventional process.

Yet other objects and advantages of the present invention will become apparent to the skilled artisan upon examination of the following detailed description of the present invention, taken in conjunction with the Figures of Drawing, wherein:

DETAILED DESCRIPTION OF THE PREFERRED EMBODIMENTS

Figure 1:
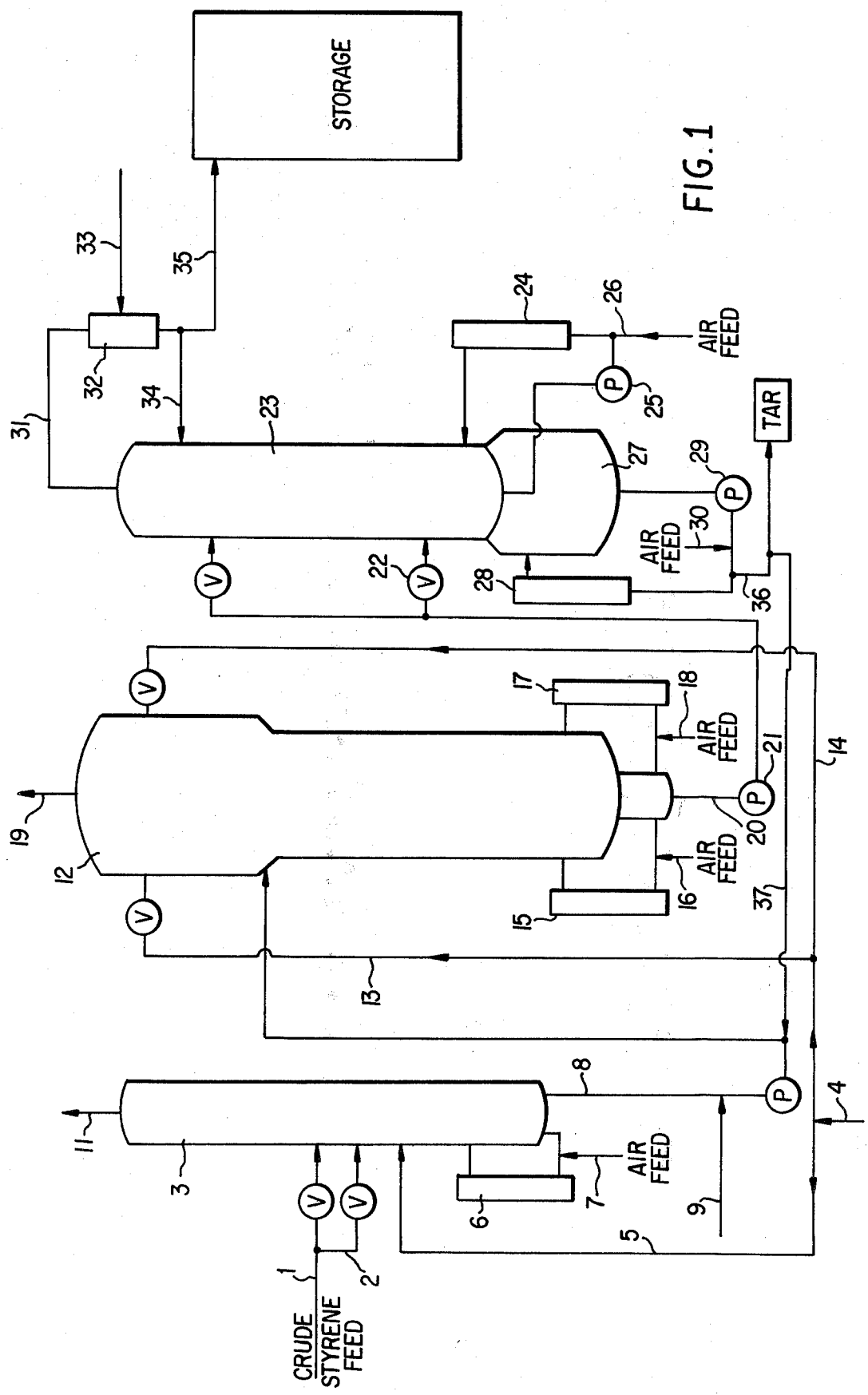
FIG. 1 is a schematic diagram of one embodiment of the present invention applied to a typical three column distillation train comprising a first fractionation column, a recycle column, and a finishing column.

The present invention provides a process for the distillation of vinyl aromatic compounds wherein the efficiency of non-volatile polymerization inhibitors is improved by optimizing the inhibitor distribution within the recycle column of a typical distillation train. Applicant has ound that approximately 80% of the polymer impurity formed during distillation is formed in the recycle column. By improving the distribution of non-volatile polymerization inhibitors within this column, practice of the present invention effects a substantial reduction in the amount of polymer formed during the distillation process. The instant invention may thus advantageously improve the efficiency of non-volatile polymerization inhibitors. However, while any non-volatile polymerization inhibitor may benefit from the instant invention, in the preferred embodiment a phenothiazine-tertiarybutylcatechol combination is employed as the inhibitor. The use of this inhibitor accrues significant advantages which make it an ideal choice for use in the present invention. Firstly, phenothiazine is relatively non-toxic as evidenced by various medicinal (veterinary) applications. Its efficiency, defined as molar ability to trap stryl radicals, is greater than 1, as compared with other conventional inhibitors having efficiencies ranging up to about 0.3. Significantly, also, the persistency of an inhibiting effect, i.e., duration of effectiveness, is also substantially greater than prior art inhibitors, the phenothiazine being synergistic with TBC. Accordingly, these properties allow for use of relatively low loadings (about 25 to about 60 ppm phenothiazine with as little as about 10 ppm to about 50 ppm tertiarybutylcatechol), relative to other known inhibitors. Moreover, use of this inhibitor combination eliminates the contamination of the reboiler bottoms of a distillation column encountered with use of certain conventional polymerization inhibitors such as sulfur. The amount of this polymerization inhibitor required for effective polymerization inhibition may vary over a wide range depending upon the conditions of distillation. Generally, the degree of stabilization is proportional to the amount of inhibitor added. In accordance with the present invention, it has been found that PZ-TBC inhibitor concentrations generally between about 5 and about 200 ppm phenothiazine in combination with about 1 ppm to about 160 ppm TBC have generally provided suitable results, depending primarily upon the temperature of the distillation mixture and the degree of inhibition desired.

The distillation process of the present invention is suitable for use virtually in any type of separation of a readily polymerizable vinyl aromatic compound from a mixture wherein the vinyl aromatic compound is subjected to a temperature above room temperature. In its most useful application, the distillation process of the present invention is applied to a distillation mixture containing one of the vinyl aromatic compounds selected from the group consisting of styrene, alpha-methyl styrene, vinyl toluene, vinyl naphthalene, divinylbenzenes, and polymer vinylbenzenes. The present invention is particularly advantageous, however, for the distillation of a crude styrene mixture.

The distillation technique of the process of the present invention is suitable for use in virtually any type of distillative separation of a readily polymerizable vinyl aromatic compound from a mixture wherein the vinyl aromatic compound is subjected to temperatures above room temperature. The process of the present invention is highly advantageous for use in atmospheric distillation techniques (i.e., open to the atmosphere). However, it is particularly advantageous for use in reduced pressure distillation techniques (vacuum distillation). In the event the reduced pressure method is employed, though, air or oxygen must be added to the system in order that the inhibitor exhibits efficacy. The efficiency of the PZ-TBC inhibitor increases with increasing oxygen concentration. The maximum amount of oxygen or air which can be added to the distillation system is governed by the need to maintain a vacuum within the system, and the need to avoid the generation of explosive atmospheres, which varies from system to system. As a general rule, the amount of air or oxygen added is sufficiently small that it does not have a substantial effect on the vacuum system. In the preferred embodiment, the vinyl aromatic compounds are preferably distilled under vacuum conditions. Typical operating conditions will include a reboiler temperature from about 65° C. to about 130° C., preferably within the range of from about 90° C. to about 115° C., and a subatmospheric pressure from about 10 to about 200 mm Hg absolute. The specific operating condiare selected to produce an overhead product of high purity vinyl aromatic monomer which generally will be above 97% and even above 99% by weight of vinyl aromatic compound, depending upon the ultimate use.

Referring to the drawings, FIG. 1 illustrates the application of the present invention to a conventional styrene distillation train comprising a benzene-toluene fractionating column 3, referred to in the industry as a B-T column, a recycle column 12, and a finishing column 23. A heated crude styrene feed is introduced into the intermediate portion of B-T column 3 through feed line 1, and optionally feed line 2. The B-T column 3 may be of any suitable design known to those skilled in the art and may contain any suitable number of vapor-liquid contacting devices, such as bubble cap trays, perforated trays, valve trays, etc.. Usually, however, column 3 contains less than 40 distillation trays. Column 3 is also equipped with a suitable reboiler 6 for supplying heat thereto.

While most of the thermal polymer is formed in the recycle column, a small but significant amount of the total thermal polymer formed during distillation is formed in the B-T column 3. Accordingly, a polymerization inhibitor is essential within this column. A feed of PZ-TBC inhibitor in a volatile aromatic hydrocarbon diluent is introduced as a separate stream into the intermediate portion of the column 3 via lines 4 and 5. Introduction of the PZ-TBC inhibitor feed at this location in the B-T column 3 will provide effective polymerization inhibition since at the lower distillation temperature of this column, the distribution of styrene is restricted to the intermediate portion thereof. Generally, effective polymerization inhibition can be achieved by providing an inhibitor distribution which is coincident with the readily polymerizable vinyl aromatic compound distribution.

The volatile aromatic hydrocarbon diluent may comprise any suitable volatile aromatic hydrocarbon in which the PZ-TBC inhibitor combination is soluble. By way of example, this diluent may include benzene, toluene, ethylbenzene, or styrene itself. Preferably, however, the volatile aromatic diluent comprises ethylbenzene since use of this diluent permits the distribution of the PZ-TBC inhibitor combination to be optimized within the recycle column as will become more apparent hereinafter.

As mentioned above, under vacuum distillation conditions, the PZ-TBC inhibitor combination requires the presence of a small amount of oxygen for activation. The oxygen employed in accordance with the present invention may be in the form of oxygen or an oxygen-containing gas. Of course, if any oxygen-containing gas is employed, the remaining constituents of the gas must be inert to the vinyl aromatic compounds undergoing distillation. The most useful, practical, and least expensive source of oxygen is, of course, air which is preferred for the present invention. As has been aforementioned, the amount of air or oxygen added to the distillation system is sufficiently small that it does not have a substantial effect on the vacuum system, i.e., the amount added is sufficiently small so as not to alter the overhead or bottoms operating temperatures. While other points of air addition may be useful, optimum effectiveness of the PZ-TBC inhibitor combination is achieved by establishing a countercurrent flow between the inhibitor and air. Accordingly, in the preferred embodiment, a stream of air is introduced through line 7 into the reboiler 6. Wherever the point of addition, though, it is essential that the air be dispersed within the distillation column. A sparger is used, therefore, for dispersing the air into the reboiler 6.

Under the distillation conditions imposed in column 3, an overhead stream comprising benzene and toluene is removed from the column via line 11. These low-boiling aromatic hydrocarbons are subsequently condensed and passed into storage for further use. The bottoms product in the B-T column, comprising styrene, ethylbenzene, inhibitor, and tar, serves as charge to the recycle column or ethylbenzene column 12 and is introduced into the intermediate portion thereof by means of line 8 and pump 10. In order to reduce the viscosity of the B-T column bottoms product, a non-volatile hydrocarbon diluent may be introduced into line 8 and thence into recycle column 12 by way of line 9. Any suitable non-volatile hydrocarbon diluent may be used, the only requirements being that the non-volatile diluent is stable and sufficiently higher boiling than styrene for ready separation by fractionation. Typical materials used for this purpose include isopropyl benzene, butylbenzene, and xylene bottoms. Preferably, however, the non-volatile hydrocarbon diluent comprises polyethylbenzene.

The recycle column 12, may be of any suitable design known to those skilled in the art and may contain from 40 to 100 trays. Preferably, however, the recycle column is of the parallel path design, i.e., two parallel distillation paths descending through the column. Additionally, it is also preferable that the recycle column contain a large number of trays, i.e., 72, in order to achieve a proper separation between the similar boiling styrene and ethylbenzene. The B-T bottoms are preferably introduced into the intermeiate portion of the recycle column 12. Heretofore, the non-volatile PZ-TBC inhibitor combination was admixed with the polyethylbenzene diluent and jointly added to the intermediate portion of the recycle column 12. While this prior method of addition provided adequate inhibitor protection to the upper portion of the recycle column 12 when a volatile inhibitor was employed, this method of addition provides less than optimum protection to the upper portion of column 12 when a non-volatile inhibitor such as PZ-TBC is employed. Moreover, adequate inhibitor protection of the upper portion of this column has been found to be essential to the elimination of thermal polymers since the high distillation temperature necessary to achieve adequate fractionation between the similar boiling ethylbenzene and styrene results in a significant distribution of styrene throughout this region. Indeed, with conventional processes which fail to provide adequate non-volatile polymerization inhibitor distribution commensurate with styrene distribution in this upper region, approximately 80% of the otal thermal polymer formed is attributable to the recycle column 12. Furthermore, polyethylbenzene cannot be present within the recycle column 12 above the intermediate portion thereof because it will be carried out of the recycle column 12 by the vaporous ethylbenzene overhead and recycled therewith to an ethylbenzene dehydrogenation reactor where it is converted to divinylbenzene, which is undesirable. Accordingly, the non-volatile inhibitor cannot be added higher into the recycle column in order to improve inhibitor distribution if it is dissolved in polyethylbenzene. In order to alleviate this problem, under the present invention, the PZ-TBC inhibitor combination is dissolved in ethylbenzene. This admixture is then introduced into the top of the recycle column, thereby improving inhibitor distribution within the critical upper region of the recycle column 12. The use of ethylbenzene as a medium for the introduction of the PZ-TBC inhibitor into the recycle column 12 accrues another significant advantage in that it does not decrease the purity of the styrene material since it is removed from the recycle column as an overhead product.

In FIG. 1, the recycle column 12 is illustrated as having a parallel path design. The admixture of PZ-TBC and ethylbenzene is introduced through lines 13 and 14, each of the distillation halves of the column 12 having an inhibitor feed line associated therewith. Each side of the distillation column 12 also has connected therewith a reboiler 15 or 17. A sparger feeds and disperses air into the reboilers 15 and 17 through lines 16 and 18.

The ethylbenzene overhead product of the recycle column 12 is withdrawn through line 19 and subsequently condensed for reuse in an ethylbenzene dehydrogenation reactor. The recycle bottoms, comprising styrene, inhibitor, polyethylbenzene diluent, and tar, is withdrawn from the reboiler area of the recycle column 12 through line 20. The recycle bottoms is then fed by pump 21 into the intermediate portion of the finishing column 23 through line 20. Optionally, the crude styrene may also be introduced into the lower portion of the finishing column 23 through line 22.

The finishing column 23 may be of any suitable design known to those skilled in the art. A typical column will contain, for example, about 24 distillation trays. A reboiler 24, preferably a forced flow reboiler, is also connected thereto in order to supply heat to the column. Due to the high viscosity of the finishing column bottoms, pump 25 is also preferably employed to circulate the bottoms through reboiler 24 and into finishing column 23. Air is introduced into the reboiler through line 26 in order to establish a countercurrent flow between air and the PZ-TBC inhibitor within the finishing column 23. Generally, inhibitor protection is adequately provided in this column by the PZ-TBC inhibitor present in the feed. Since, however, inhibitor is gradually removed from the distillation system, in order to insure adequate inhibitor protection throughout the distillation train, the PZ-TBC inhibitor in ethylbenzene is continuously added to the system through lines 5, 13, and 14. Conventionally, moreover, TBC is admixed with the high purity styrene overhead product in reflux accumulator 32, through line 33, and a portion of this mixture is returned to the finishing column 23 as reflux through line 34, providing thereby further protection against polymerization.

The high purity styrene overhead product withdrawn through line 31 from the finishing column 23 will generally be above 97% and even above 99% by weight styrene, depending upon the ultimate use. As has been mentioned, the high purity styrene overhead product is admixed with TBC in reflux accumulator 32. The majority of this product is withdrawn through line 35 to storage to await its ultimate use. The finishing column bottoms product is composed of polystyrene, undistilled styrene, polyethylbenzene, and the PZ-TBC inhibitor. This fraction is withdrawn from the finishing column 23 into batch pot 27 for further processing. The batch pot 27 is shown as comprising a bottom section of the finishing column 23. However, it should be obvious to those skilled in the art that a separate unit could also be used. Reboiler 28 supplies heat to the bottoms product, which is circulated by pump 29. Sparger air feed 30 introduces and disperses air into the reboiler circuit to activate the PZ-TBC inhibitor. The tar produced in the batch pot 27 is withdrawn from the system on a continuous basis through line 36. In one particularly preferred embodiment of the present invention, a portion of the tar, containing substantial amounts of PZ-TBC inhibitor, is recycled through line 37 for introduction into the recycle column 12 through line 8 in order to conserve the PZ-TBC inhibitor. Through the recycling of the PZ-TBC containing tar, the PZ-TBC inhibitor may thus be reused, accruing thereby a significant reduction in the inhibitor process requirements.

Figure 2:
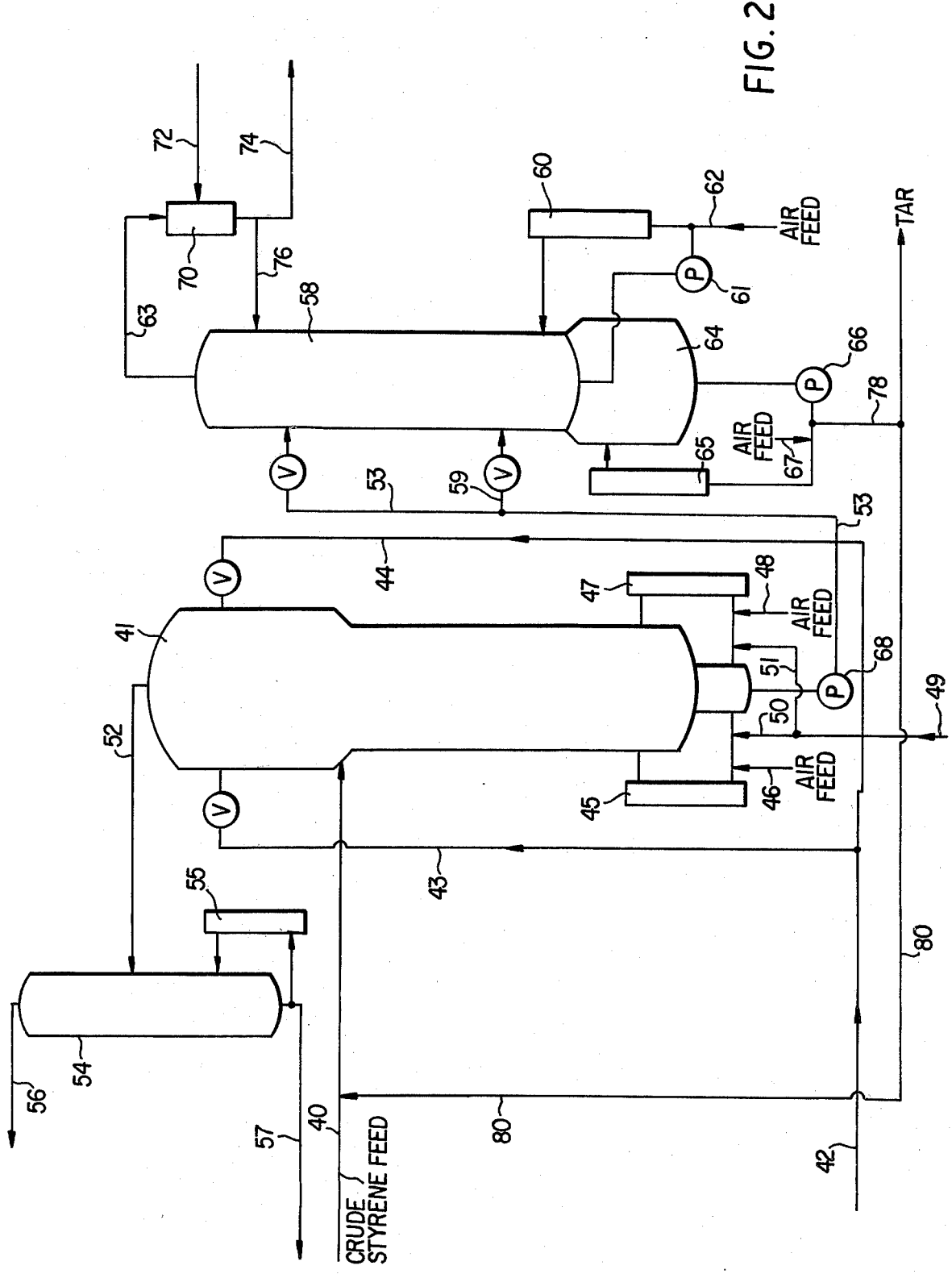
FIG. 2 is a schematic diagram of the present invention applied to another common distillation train in which a crude vinyl aromatic compound feed is introduced directly into the recycle column wherein the lower boiling components are removed as one overhead fraction and subsequently separated in an off-stream column.

FIG. 2 illustrates the application of the process of the present invention to another typical distillation train for styrene. A styrene feed is introduced into the intermediate portion of recycle column 41, which is preferably of the parallel distillation path design. Line 42 supplies the PZ-TBC inhibitor in ethylbenzene as a separate stream to each distillation path through the two divergent feed lines 43 and 44. A countercurrent flow of inhibitor and air is established by introducing and dispersing an air feed through lines 46 and 48 into reboiler circuits 45 and 47, respectively. Preferably, a polyethylbenzene diluent is introduced into the reboilers 45 and 47 through line 49 and divergent feed lines 50 and 51.

An overhead product comprising benzene, toluene, and ethylbenzene is withdrawn through line 52 for subsequent fractionation in distillation column 54. In column 54, benzene and toluene are withdrawn as an overhead fraction and are subsequently condensed for further use. An ethylbenzene bottoms product is withdrawn through line 57 and recycled for use in an ethylbenzene dehydrogenation reactor. Reboiler 55 provides the B-T bottom 54 with the necessary heat for distillation. Since no polymerizable vinyl aromatic material is present in the B-T column 54, the presence of inhibitor is unnecessary.

The recycle bottoms product, comprising polystyrene, undistilled styrene, polyethylbenzene, and PZ-TBC inhibitor is withdrawn from recycle column 41 through line 53. The crude styrene is then charged to the upper portion of the finishing column 58 by means of pump 68. Optionally, crude styrene may be introduced into the lower region of the finishing column 58 through line 59. A reboiler circuit comprising reboiler 60, pump 61 and air feed line 62 is attached to the finishing column 58 for supplying the necessary heat and for establishing a countercurrent flow of activating air and inhibitor within the column. The purified styrene overhead product is withdrawn through line 63 to the reflux accumulator 70 wherein it is mixed with TBC from line 74. A portion of this product is recycled through line 76 for addition to the finishing column 58 as reflux. The major portion of the purified styrene is withdrawn through line 74 to storage.

The finishing column bottoms product is directed to batch pot 64 for further processing. Batch pot 64 has connected thereto a suitable reboiler circuit comprising forced flow reboiler 65, pump 66, and air feed 67 to facilitate the further fractionation of the bottoms. The tar produced during the distillation process is withdrawn through line 78. In the preferred embodiment, a portion of this tar is recycled to the recycle column 41 through line 80 in order to conserve inhibitor.

Use of the distillation process of the present invention thus enables a distillation apparatus to operate in an increased rate as opposed to conventional prior art processes since the efficiency of non-volatile inhibitors is improved over that provided by conventional processes. By increasing the distribution of the non-volatile inhibitor within the upper portion of the recycle column to correspond with the locus of distribution of the vinyl aromatic compound, the amount of thermal polymer formed is substantially reduced over that occurring in conventional distillation processes. Consequently, higher distillation temperatures and higher pressures may be utilized without the formation of objectional amounts of thermal polymer. In this manner, the rate of distillation may be increased without increasing the amount of polymerization which has been deemed to be acceptable in accordance with conventional distillation procedures.

In order to more fully described the present invention, the following example is presented which is intended to be merely illustrative and not in any sense limitative of the invention.

EXAMPLE

A styrene distillation train is operated in accordance with the distillation process of the present invention and in accordance with a conventional procedure, using a PZ-TBC polymerization inhibitor. Samples are periodically removed from the finishing column and their viscosity is measured at 195° F. A sample produced in accordance with a conventional distillation process exhibits a viscosity of more than five times the viscosity of a sample produced in accordance with the instant invention, corresponding to over twice the tar manufactured per day of the instant distillation process. It is thus seen from this example that by improving the distribution of a non-volatile PZ-TBC inhibitor within the upper portion of a recycle column, significant reductions in the amount of thermal polymer can be accrued over that produced in conventional distillation processes.

While the invention has been described in terms of various preferred embodiments and illustrated by example with respect thereto, the skilled artisan will appreciate that various modifications, substitutions, omissions, and changes may be made without departing from the spirit thereof. Thus, for example, while the present invention has been emphasized for use with a PZ-TBC inhibitor combination, another non-volatile polymerization inhibitor, such as sulfur, might be employed without departing from the scope of the present invention, albeit, PZ-TBC is the most preferred of these polymerization inhibitors. Accordingly, it is intended that the scope of the present invention be limited solely by that of the following claims:

What is claimed is:

1. A process for the distillation of a readily polymerizable vinyl aromatic compound employing as a polymerization inhibitor the combination of phenothiazine ($C_{19}H_9NS$) and tertiarybutylcatechol (TBC), comprising the steps of:
   (a) introducing a feed of impure vinyl aromatic compound into a distillation train containing a recycle column and a finishing column, said feed being introduced into the recycle column;
   (b) introducing as a separate stream into the upper portion of said recycle column an effective polymerization inhibiting amount of said inhibitor combination in a volatile aromatic hydrocarbon diluent; and,
   (c) distilling said feed under distillation conditions in the presence of oxygen to recover from the finishing column of said distillation train an overhead product of high purity vinyl aromatic compound and a residual bottoms fraction.

2. The process of claim 1, further comprising the steps of subjecting said impure feed to distillation in the presence of an effective amount of said inhibitor combination and oxygen to remove a first boiling fraction prior to introduction into said recycle column.

3. The process of claim 1, wherein said compound is distilled under reduced pressure distillation conditions.

4. The process of claim 3, wherein said reduced pressure distillation conditions comprise a temperature between about 65° and 130° C.

5. The process of claim 3, wherein said reduced pressure distillation conditions comprises a temperature between about 90° and 115° C.

6. The process of claim 1, wherein said vinyl aromatic compound is styrene.

7. The process of claim 1, wherein said inhibitor system is continuously added to said distillation train.

8. The process of claim 1, wherein said volatile aromatic hydrocarbon diluent is ethylbenzene.

9. The process of claim 1, wherein said oxygen is supplied by air continuously introduced and dispersed into the reboiler portion of said distillation system.

10. The process of claim 1, wherein said inhibitor combination is present in said distillation system in an amount of from about 5 ppm to about 200 ppm phenothiazine and from about 1 ppm to about 160 ppm TBC by weight of said vinyl aromatic compound.

11. The process of claim 1, further comprising introducing a relatively non-volatile hydrocarbon diluent into said distillation train.

12. The process of claim 11, wherein said non-volatile hydrocarbon diluent is polyethylbenzene.

13. The process of claim 1, wherein a portion of said residual bottoms fraction is recycled back into said distillation train.

* * * * *